United States Patent [19]

Kuleza et al.

[11] Patent Number: 5,248,494
[45] Date of Patent: Sep. 28, 1993

[54] METHOD OF REDUCING ANTHRALIN INDUCED INFLAMMATION AND STAINING

[75] Inventors: John E. Kuleza, Berlin, Conn.; Lawrence Clifford M.; Sam Shuster, both of Newcastle Upon Tyne, United Kingdom

[73] Assignee: Young Pharmaceuticals Inc., Wethersfield, Conn.

[21] Appl. No.: 896,217

[22] Filed: Jun. 10, 1992

[51] Int. Cl.$^5$ .......................... A61K 9/08; A61K 9/12
[52] U.S. Cl. ......................................... 424/45; 424/47; 424/78.02; 424/78.03; 424/78.05; 514/663; 514/667; 514/671; 514/732; 514/863; 514/887; 514/974
[58] Field of Search ............ 424/45, 47, 78.02, 78.03, 424/78.05; 514/663, 671, 667, 732, 863, 887, 974

[56] References Cited

U.S. PATENT DOCUMENTS

| | | | |
|---|---|---|---|
| 4,363,815 | 12/1982 | Yu et al. | 514/263 |
| 4,513,011 | 4/1985 | Grollier et al. | 514/730 |
| 4,608,392 | 8/1986 | Jacquet et al. | 514/772 |
| 4,796,812 | 1/1989 | Grollier | 239/303 |
| 4,826,677 | 5/1989 | Mueller et al. | 424/78.05 |
| 4,868,219 | 9/1989 | Thornfeldt | 514/663 |
| 5,061,486 | 10/1991 | Whitefield | 514/732 |

OTHER PUBLICATIONS

Ramsay et al, "Reduction of anthralin-induced inflammation by application of amines", J Am Acad Dermatol 1990; 22765-772.

Ramsay et al, "The effect of triethanolamine application on anthralin-induced inflammation and therapeutic effect in psoriasis", J Am Acad Dermatol 1990; 23:73-6.

B. Ramsay, C. M. Lawrence, J. M. Bruce and S. Shuster, "Reduction of anthralin inflammation by application of topical amine compounds", British Journal of Dermatology, 1987, 118: 278.

C. M. Lawrence, S. Shuter, M. Collins and J. M. Bruce, "Reduction of anthralin inflammation by potassium hydroxide and Teepol", British Journal of Dermatology, 1987, 116: 171-177.

*Primary Examiner*—Thurman K. Page
*Assistant Examiner*—Robert H. Harrison
*Attorney, Agent, or Firm*—Chilton, Alix & Van Kirk

[57] ABSTRACT

A lenitive composition is provided for application to the skin of an anthralin patient for reducing anthralin-induced inflammation and the staining associated with anthralin use. The lenitive composition is a single phase aqueous treating solution comprising an organic amine and a film-forming agent dissolved within a nontoxic dermatologically acceptable carrier. The organic amine is selected from the group consisting of lower alkyl and lower alkanol primary, secondary and tertiary amines and comprises about 1 to 25 percent by weight of the single phase aqueous treating solution. The solution is topically applied to the anthralin-treated areas so as to completely cover the treated areas. The solution is applied before or after anthralin wash off, preferably in the form of a fine spray or mist.

16 Claims, No Drawings

METHOD OF REDUCING ANTHRALIN INDUCED INFLAMMATION AND STAINING

The present invention relates generally to a lenitive composition and method for reducing staining and skin irritation associated with anthralin treatment of psoriasis.

BACKGROUND AND SUMMARY OF THE INVENTION

Psoriasis is an inherited, chronic, proliferative disease characterized by epidermal hyperplasia and inflammation. The disease is characterized by the presence of psoriatic lesions that appear as erythematous, circumscribed plaques covered by loosely adherent silvery scales. The lesions may become extensive and may involve any area of the body, although lesions most often appear on the elbows, knees and scalp. Although the psoriatic plaques usually remain localized, in some cases the disease is sufficiently widespread as to be incapacitating and may be prolonged and unpredictable. Although many treatments for psoriasis provide limited relief, a common treatment for psoriasis involves topical application of corticosteroids, sometimes with occlusive dressings. However, the benefits of such treatments must be balanced against their adverse effects which can include skin atrophy with telangiectasia and striae formation as well as adrenal suppression.

An extremely effective treatment for moderate to severe psoriasis involves topical application of a compound called anthralin (1, 8-dihydroxyanthrone). Beneficially, anthralin has no substantiated systemic toxic or carcinogenic effects and provides a more prolonged remission than is usually evidenced by topical corticosteroids. Anthralin is usually incorporated into cream or ointment dosage forms for skin application at concentrations ranging from 0.1 percent to about 8 percent. The therapeutic effects of anthralin appear to require only a short contact with the psoriatic lesions and may be applied daily for periods of 15 to 60 minutes and then washed off with soap and water. Unfortunately, anthralin is not widely used because of its ability to irritate the perilesional skin and its tendency to stain the hair, skin and nails of the patient, as well as any fabrics or bathroom fixtures that come in contact with the anthralin composition. The resultant staining leaves a deep violaceous color and these side effects have reduced the acceptance of this treatment.

Accordingly, it is an object of the present invention to provide a lenitive composition for application to the skin of an anthralin patient for reducing anthralin-induced inflammation and the staining associated with anthralin use. Included in this object is the provision for a composition for reducing the staining of skin, hair and nails and the skin irritation associated with anthralin treatment of psoriasis. A further advantage of the composition and method of the present invention is the provision for reducing or preventing the staining of fabrics, particularly pajamas and bedclothes, as well as bathroom fixtures as a result of anthralin treatment of psoriasis.

A further object of the present invention is to provide a lenitive composition of the type described that can be applied as a single phase aqueous treating solution that can be easily applied and removed from the effected areas of the skin.

It has been reported by Ramsay et al that anthralin-induced inflammation may be reduced by the application of certain organic amines. J. Am. Acad. Dermatol. 1990, Vol. 22, pages 765-772 and Vol. 23, pages 73-76. In those publications, it is noted that while anthralin therapy is effective even with short contact, inflammation of the perilesional skin is a problem. Accordingly, dilute potassium hydroxide has been used to deactivate the anthralin and has led to a reduction in anthralin-induced inflammation, but not in its therapeutic effect. Because potassium hydroxide is also an irritant, the publications evaluated the use of certain organic amines, namely alkylamines and alkanolamines for a similar inhibitory effect on anthralin-induced inflammation. The amines were used as solutions dissolved in dichloromethane. However, dichloromethane is used in cleaning fluids and its human toxicity is known to be narcotic in high concentrations. Additionally, triethanolamine was used in an emulsion at an amine concentration of 10 percent by weight. However, the residual effect of the emulsion on the skin of the patients hampers the therapeutic action of subsequent anthralin treatments.

Accordingly, it is another object of the present invention to provide a new and improved lenitive composition containing the effective organic amines and a film former in an aqueous non-toxic and dermatologically acceptable carrier.

Other objects, features and advantages will be in part obvious and in part pointed out more in detail hereinafter.

These and related objects are achieved in accordance with the present invention by providing a lenitive composition for application to the skin of an anthralin-treated patient for reducing anthralin-induced inflammation and the staining associated with anthralin use comprising a single phase aqueous treating solution comprising an organic amine and a film-forming agent dissolved within a nontoxic dermatologically acceptable carrier. The organic amine is selected from the group consisting of lower alkyl and lower alkanol primary, secondary and tertiary amines and comprises about 1-25 percent by weight of the single phase aqueous treating solution. The solution is topically applied to the anthralin-treated areas so as to completely cover the treated areas. The solution is applied after anthralin wash off and is permitted to dry, but can also be applied before wash off as well, preferably in the form of a fine spray or mist.

A better understanding of the objects and advantages of the invention will be obtained from the following detailed description which sets forth an illustrative embodiment and is indicative of the way in which the principles of the invention are employed, including the several steps of the method and the relation of one or more of such steps with respect to each of the others and the composition possessing the features, characteristics, properties and relation of elements described and exemplified herein.

DESCRIPTION OF A PREFERRED EMBODIMENT

As mentioned hereinbefore, the lenitive composition of the present invention is a single phase aqueous treating solution and consists essentially of an effective amount of one or more selected organic amines and a film-forming agent dissolved in a nontoxic dermatologically acceptable carrier. The organic amines are selected from the group consisting of lower alkyl and lower alkanol primary, secondary and tertiary amines wherein the lower alkyl group contains 4-18 carbon atoms and the lower alkanol group contains 2-12 carbon atoms. Among these, the most effective alkyl amines are those having an alkyl chain of 6-8 carbon atoms, while the most effective alkanol amines are those having an alkyl chain of 2-4 carbon atoms. Accordingly, in the preferred composition, the organic amine is selected from the group consisting of octylamine, octadecylamine, dihexylamine, trihexylamine, trioctylamine, ethanolamine, DL-1-amino-2-propanol, diisopropanol amine and triethanolamine.

The amount of the organic amine should be sufficient to be effective in the composition of the present invention and typically is present in greater amounts than the film-forming agent. Specifically, the organic amine comprises up to about 25 percent by weight of the single phase aqueous treating solution and preferably about 1 and 15 percent by weight. Most effective results are achieved in the range of from 3-10 percent by weight of the organic amine.

The film-forming agent used in the composition of the present invention is intended to ensure a uniform coating of the organic amine over the entire effected surface to which it is applied. The agent should be nontoxic, dermatologically acceptable and exhibit the ability to form continuous or nearly continuous sheetlike molecular networks or matrices over surfaces to which the composition is applied. Of course, it should be water soluble and must also be compatible with the organic amines employed as the principal components of the treating solution. In this connection, it has been found that low molecular weight water soluble polymers, particularly cellulose derivatives such as cellulose ethers, will produce good results in the solutions of the present invention. In this connection, materials such as methylcellulose, hydroxypropyl methylcellulose, hydroxybutyl methylcellulose, hydroxyethyl cellulose and hydroxypropyl cellulose may be employed as well as other water soluble polymeric materials, such as the pharmaceutical grade of polyvinylpyrrolidone sold by GAF under the trademark "Plasdone". As will be appreciated, other film-forming materials known to those skilled in the arts of pharmacological and cosmetic compositions also may be employed. In general, the lower molecular weight grades of the polymeric materials will produce film-forming solutions of lower viscosity than the higher molecular weight materials at a given concentration.

The amount of film-forming agent employed typically is less than the amount of organic amine on a weight basis. For example, the film-forming agent may comprise from about 0.1 to 10 percent by weight and preferably about 0.5 to 5 percent of the lenitive solution. Relative to the amine, the film-forming agent is usually about one half that of the amine or less. Good results have been achieved at amine to film-forming agent ratios ranging from 2:1 to 20:1 with most formulations having a ratio of 3:1 to 12:1 and preferably 5:1 to 10:1.

The solvent for the organic amine and film-forming agent is preferably either water or an aqueous solution capable of dissolving the amine and film-forming agent so as to provide the desired single phase aqueous treating solution. As indicated, the carrier should be a nontoxic dermatologically acceptable solvent that is primarily water based, although it may contain certain organic ingredients. Where the solvent is only water, it is preferably purified either by distillation or deionization so as to avoid the introduction of trace amounts of reactants into the composition. For certain of the amines, it may be preferable to initially dissolve the material in an organic solvent followed by subsequent dissolution or dilution with the aqueous carrier. Such organic materials, of course, also must be nontoxic and dermatologically acceptable and should ensure complete solubility of the amine with a wide range of storage and usage temperatures. Where organic solvents are employed, these generally fall into the category of alcohols and glycols. For example, solvents such as ethanol, isopropanol or propylene glycol may be employed effectively. As will be appreciated, repeated applications of certain organic solvents to the skin may compromise its protective barrier properties and thus cause skin dryness and/or irritation. Accordingly, the preferred composition of the invention should contain a minimum amount of organic solvent needed to adequately solubilize the organic amines.

As will be appreciated, additional ancillary materials may be added to the composition to impart a particular desired characteristic. These are typically presently in relative small quantities, that is less than 5 percent and preferably only about 0.1 to 3 percent by weight. Enhanced spreading, adhesion and penetration can be achieved by the use of organic and nonorganic surfactants. These materials aid in solubilizing the organic amines or the film-forming agent in the aqueous carrier solution. Representative materials include anionic sodium lauryl sulfate, nonionic ethoxylated fatty ethers such as POE(10) oleyl ether and cationic cetalkonium chloride. In addition, fragrances or perfumes may be added to impart an appropriate fragrance to the treating solution. Additionally, emollients and skin protectants may be incorporated to counteract skin dryness. Such emollients include glycerin, sorbitol and methylglucose ethers, allantoin and similar materials. Finally, preservatives, such as antibacterial and antifungal agents, may also be employed. These may include materials such as benzyl alcohol and chloroxylenol. As will be appreciated, one or more of these elective ingredients or similar elective materials may be added in a manner well known to those skilled in the art.

The treating solution is formulated by initially measuring or weighing out the necessary ingredients and thoroughly mixing the amine and the film-forming agent with water or an aqueous solution of the organic solvent until the solution is clear. In certain instances such as with various cellulose ethers which compete with other solutes for the solvent, it is preferred to initially dissolve the film-forming agent in the solvent carrier and then add other ingredients after a clear solution is obtained. In those instances where an organic amine has better solubility in an organic solvent than in pure water, it is preferred to first dissolve the amine in the organic solvent portion of the solvent carrier and then slowly add this solution to the balance of the composition to achieve the desired composition and concentration.

The compositions of the present invention are applied topically to the anthralin-treated areas of the skin including both the psoriatic lesions and the perilesional skin adjacent thereto. Since the anthralin treatment is effective within only a brief period of time, the anthralin is typically washed off the skin after a contact period of between 10-60 minutes. For best results, it is generally desirable that the skin be gently patted dry with a towel to absorb most of the wash water prior to application of the lenitive composition of the present invention. This will prevent dilution of the composition and provide for the most beneficial result.

The lenitive composition of the present invention is liberally applied to the anthralin treated areas and may be simply poured over the skin or spread thereon with the aid of cotton swabs, balls, pads or similar applicators, or simply by the use of the patient's fingertips. Advantageously, the composition also may be sprayed onto the skin by converting the composition into a fine spray or mist. This can be accomplished by either combining the composition with a suitable propellent and packaging the resultant mixture in a container fitted with a valve-type closure that converts the pressurized contents to an aerosol spray or mist or, alternatively, by packaging the composition in containers fitted with a closure which, via a mechanical pumping action, forces the liquid contents through an aperture or orifice designed to convert the liquid contents into an atomized spray or mist.

An advantageous feature of the present invention is that it does not adversely impact on the therapeutic effect of the anthralin treatment even though it is applied to the psoriatic lesions. This suggests that the irritation and staining associated with the anthralin treatment of psoriasis can be disassociated from its therapeutic effect and preferably, the lenitive composition can simply be allowed to dry on the skin after it is applied so that it will remain thereon until the next application of the anthralin preparation. As mentioned, the composition is effective in reducing the staining of fabric, particularly bedclothes and pajamas worn following the anthralin preparation washoff. This effect may be due to the rapid oxidation and fixation on the skin by the anthralin incompletely removed during the washoff procedure.

In accordance with the preferred treating method, the lenitive composition of the present invention is first applied approximately 2 minutes or so before the anthralin preparation is washed off the patient. Where this first application is employed, preferably as a mist or spray, care must be taken not to smear the anthralin preparation already applied to the psoriatic lesions to additional perilesional skin areas. The purpose of the first application is simply to form a coating of the lenitive composition over the perilesional skin and hair, thereby protecting those areas from the anthralin preparation as it is smeared or rubbed off the psoriatic lesions during the washoff process. The first application of the lenitive composition prior to washing off the anthralin is combined with a second application of the lenitive composition following washoff, as described hereinbefore. Accordingly, the composition of the present invention is applied twice, once prior to washoff and a second time after the anthralin has been washed from the patient's treated areas.

A further beneficial result of the composition of the present invention is the substantial reduction in staining of bathroom fixtures such as porcelain, enamel, ceramic tiles and tile grout which often occurs when anthralin preparations are washed off the body. Although this effect is not fully understood, it is believed that the lenitive composition facilitates rapid oxidation of the anthralin before it is deposited on those tub and shower surfaces during the washing off process.

In those instances where the anthralin treatment must be applied to the scalp, the procedure is substantially the same. It is frequently desired to assure full and complete contact of the lenitive composition with the hair shafts by combing or brushing the composition into the hair in a full and complete manner, preferably after shampooing, to remove the anthralin preparation. Once again, where shampooing occurs before treatment with the lenitive composition, it is desired to remove excess water on the hair and scalp prior to using the composition, thereby avoiding dilution thereof. The lenitive composition may be permitted simply to dry on the hair or scalp after it has been applied and may remain there until the next application of the anthralin preparation.

In order that the present invention may be more readily understood, it will be further described with reference to the following specific examples which are given by way of illustration only and are not intended to be a limit on the practice of the invention:

EXAMPLE I

A lenitive solution was prepared by mixing 12 parts by weight triethanolamine, 1 part by weight hydroxypropyl cellulose having a molecular weight of about 100,000, 0.7 parts by weight of benzyl alcohol, 0.7 parts by weight of the surfactant POE (10) oleyl ether and 85.6 parts by weight of distilled water.

A patient having chronic plaque psoriasis with 25% involvement was treated daily for three weeks as follows: A 1% anthralin cream, available under the name "Drithocreme HP", was applied to the psoriatic area of the skin and allowed to remain for twenty minutes. Before removing the anthralin, one-half of the treated area was sprayed with the above lenitive solution. The patient then washed and dried the entire anthralin-treated area. The lenitive solution was again sprayed onto the same half of the treated area and allowed to dry.

The anthralin-related inflammation and staining was graded on a scale of 0 to 4 with 0 being "none" and 4 being "severe". After three weeks, inflammation and staining were graded as mild (value of 1) in the half treated with lenitive solution and substantial (value of 3) in the untreated area. Plaque clearance and thickness improved significantly and there was no difference in clearance and thickness between the half treated with lenitive solution and the untreated half.

The same procedure was applied to a second patient. However, the 1% anthralin cream was used alone for the first two months of treatment and the lenitive solution was applied to the entire anthralin-treated area during the next two months. Prior to use of the lenitive solution, considerable rust-like staining of the shower took place. However, after two months of use of the lenitive solution with a different shower facility, no staining appeared.

EXAMPLE II

A lenitive solution was prepared from 12 parts by weight diisopropanolamine, 4 parts by weight polyvinylpyrrolidone having a molecular weight of about 30,000 and 84 parts by weight of distilled water.

A patient having chronic plaque psoriasis with 30% involvement was treated daily for three weeks as follows: A 1% anthralin cream (Drithocreme HP) was applied to the psoriatic area of the skin and allowed to remain for 20 minutes. It was then washed off and the skin patted dry with an absorbent towel. About two minutes after drying, one half of the anthralin-treated area was treated with the above lenitive solution using a cotton ball applicator. The solution then was allowed to dry.

The inflammation and staining was graded in the same manner as Example I. After three weeks the inflammation was graded as none (value of 0) and the staining was graded as mild (value of 1) in the lenitive solution treated area and substantial (value of 3) in the untreated area. As in Example I, the lenitive solution did not impact on the effect of the anthralin treatment on plaque clearance and thickness.

EXAMPLE III

A lenitive solution was prepared from 3 parts by weight of ethanolamine, 3 parts by weight of octadecylamine, 1 part by weight of hydroxyethyl cellulose having a molecular weight of about 90,000, 5 parts by weight of sorbitol, 1 part by weight of benzyl alcohol, 15 parts by weight of ethanol, 3 parts by weight of a surfactant and the remainder, 69 parts by weight, of deionized water.

The procedure of Example II was used on a patient with chronic plaque psoriasis with 35% involvement using a 2% anthralin ointment and the above lenitive solution.

The stronger anthalin treatment resulted in higher levels of inflammation and staining in the untreated areas and a more dramatic reduction of those properties in the lenitive treated area. Significant bathtub staining was observed.

EXAMPLE IV

A lenitive solution was prepared using varying amounts of diisopropanolamine and polyvinyl pyrrolidone having a molecular weight of about 30,000 in distilled water.

The lenitive solutions were applied by spray to anthralin-treated patients and inflammation and degree of staining was measured using the following procedure.

The clinically normal flexor forearm skin of volunteer subjects was treated with anthralin at separate paired sites on each forearm. The anthralin was applied as a 1% anthralin cream at a rate of 20 mg over an area of approximately 1 square centimeter. After twenty minutes the anthralin sites were washed and patted dry with an absorbent towel. The lenitive solution was applied by spraying and the skin was allowed to dry. The sites were then covered for protection.

Anthralin inflammation was measured by an increase in skin thickness determined with Harpenden calipers using measurements taken prior to and 48 hours after treatment with the lenitive formulations.

The degree of staining was assessed under identical lighting conditions using the following scale based on the Pantone Color Matching System: (0) - none, (1) - slight, (2) - moderate, (3) - substantial, (4) - deep.

TABLE 1

|  | Sample | | | |
| --- | --- | --- | --- | --- |
|  | 4-A | 4-B | 4-C | 4-D |
| Amine (%) | 12 | 25 | 12 | 12 |
| Film-former (%) | 4 | 4 | 0.1 | 10 |
| Water (%) | 84 | 71 | 87.9 | 78 |
| Skin Thickness Difference (%) | 74 | 81 | 69 | 76 |
| Stain |  |  |  |  |
| untreated area | 3 | 3 | 3 | 2 |
| treated area | 0 | 0 | 1 | 0 |

The higher amount of amine produced a slightly better result except that greater flaking and irritation of the skin was noted. The reduced film-former of Sample 4-C was slightly less effective and the formulation of Sample 4-D was slightly sticky.

EXAMPLE V

The procedure of Example IV was followed using the following lenitive solution:

| Component | Amt. (%) by weight |
| --- | --- |
| Dihexylamine | 6 |
| Glycerin | 2 |
| Hydroxypropyl methylcellulose (10K mol. wt.) | 3 |
| Benzyl alcohol | 1.5 |
| Ethanol | 10 |
| Water | 67.5 |

The reduction of inflammation, as measured by the skin thickness difference, is 96% with staining assessed at a value of 3 for the untreated areas and 0 for the amine treated areas.

EXAMPLE VI

A lenitive solution was prepared from 3 parts by weight of triethanolamine, 1 part by weight of hydroxypropyl cellulose having a molecular weight of about 100,000 and 96 parts by weight of distilled water.

The clinically normal flexor forearm skin of three volunteer subjects was treated at four separate paired sites on each forearm by pipetting 0.1% and 0.2% chloroform solutions of anthralin into a glass well applied to skin sites measuring 12 mm in diameter. The concentration of anthralin was 0.1% at two paired sites and 0.2% at the other two paired sites.

Five minutes after anthralin application, a 20 ul volume of the above lenitive solution, Solution I, was pipetted onto two sites on each forearm. An equivalent volume of a 3 percent by weight solution of triethanolamine in dichloromethane, Solution II, was applied to the remaining two anthralin treated sites on the same forearm. The skin was allowed to dry and the sites were occluded with a protective covering of transparent Saran Wrap (polyvinylidene chloride film). Inflammation was measured after 48 hours and staining after 72 hours.

TABLE 2

|  | Sample No. | | | |
| --- | --- | --- | --- | --- |
|  | 6-A | 6-B | 6-C | 6-D |
| Anthralin (conc.) | 0.1 | 0.1 | 0.2 | 0.2 |
| Solution | I | II | I | II |
| Skin thickness diff. (%) |  |  |  |  |
| Subject 1 | 87 | 79 | 76 | 70 |
| Subject 2 | 85 | 77 | 78 | 68 |
| Subject 3 | 88 | 80 | 77 | 71 |
| Staining |  |  |  |  |
| Subject 1 | — | — | 1 | 2 |
| Subject 2 | — | — | 1 | 1 |
| Subject 3 | — | — | 2 | 2 |

All three subjects showed a dose dependent increase in inflammation with treated sites showing a smaller increase than non-treated sites. Staining of untreated sites at the 0.2% anthralin concentration level for the three subjects were 3, 3 and 4 respectively. Based on the test results, the formulation using the film-former provided greater inflammation reductions and reduced staining relative to the dichloromethane solution.

EXAMPLE VII

A lenitive solution similar the Example VI was prepared using 10 parts by weight triethanolamine and 1 part by weight hydroxypropyl cellulose.

Anthralin in a hydrophilic ointment with 0.5% salicylic acid was applied daily to three patients with chronic plaque psoriasis. The concentration of anthralin started at 1% and was increased every three days to a maximum of 4% over a period of four weeks. The anthralin was washed off 20 minutes after application.

After wash off, the above lenitive solution was sprayed on one half of the anthralin treated area and the other half was treated with an aqueous cream containing 10% by weight of triethanol amine, care being taken not to overlap the treatments. Both treatments remained on the skin without washing until the next anthralin treatment 24 hours later. The patients were assessed weekly for plaque severity, plaque extent and plaque thickness. The results are set forth in Table 3.

TABLE 3

| Week | Mean Clearance | | Mean Extent | | Mean Thickness | |
|---|---|---|---|---|---|---|
| | Solution Side | Cream Side | Solution Side | Cream Side | Solution Side | Cream Side |
| 0 | 2.8 | 2.8 | 35% | 35% | 0.52 mm | 0.52 mm |
| 1 | 1.5 | 2.0 | 21% | 32% | 0.26 mm | 0.45 mm |
| 2 | 1.0 | 1.5 | 15% | 22% | 0.22 mm | 0.40 mm |
| 3 | 0.75 | 1.25 | 12% | 18% | 0.20 mm | 0.35 mm |
| 4 | 0.6 | 1.0 | 12% | 14% | 0.21 mm | 0.29 mm |

While clearance was observed in all patients, the solution side showed more rapid reduction in plaque severity, extent and thickness.

EXAMPLE VIII

A lenitive solution was prepared from 10 parts by weight of octylamine, 5 parts by weight of polyvinylpyrrolidone having a molecular weight of about 15,000, 0.2 parts by weight of cetalkonium chloride, 30 parts by weight of isopropanol and 54.8 parts by weight of distilled water.

A patient having chronic plaque psoriasis of the scalp was treated according to the procedure of Example I using cream having an anthralin concentration of 0.5%. The inflammation as well as the scalp and hair staining dropped from a level of 2 for the untreated area to a level of 0 for the area treated with the lenitive solution. The elimination of hair staining is particularly significant for individuals whose natural hair color is a light shade or white.

While the preferred embodiment of the invention has been set forth for purposes of illustration, it is apparent to persons skilled in the art that various modifications, adaptations and variations of the foregoing specific disclosure can be made without departing from the spirit and scope of the teachings of the present invention.

We claim:

1. A method of reducing anthralin-induced inflammation and the staining associated with anthralin use comprising the steps of providing a single phase aqueous treating solution comprising at least one organic amine and a non-toxic dermatologically acceptable water soluble film-forming polymer dissolved within a non-toxic dermatologically acceptable carrier, the organic amine being selected from the group consisting of lower alkyl and alkanol primary, secondary and tertiary amines and comprising about 1-25 percent by weight of the single phase treating solution, the polymer comprising about 0.1-10 percent by weight of the solution, and topically applying the aqueous treating solution to anthralin treated areas of human skin.

2. The method of claim 1 wherein the solution is applied following a step of washing the anthralin from the treated areas.

3. The method of claim 1 wherein the solution is applied prior to a step of washing the anthralin from the treated area.

4. The method of claim 1 wherein the treating solution is applied using a fine spray or mist.

5. The method of claim 1 wherein the treating solution dries on the treated areas.

6. The method of claim 1 wherein the solution is applied prior to and after a step of washing the anthralin from the treated area.

7. The method of claim 6 wherein excess liquid is removed from the treated area prior to the second application of the treating solution.

8. The method of claim 1 wherein the lower alkyl group of the organic amine contains 4-8 carbon atoms and the lower alkanol group of the amine contains 2-12 carbon atoms.

9. The method of claim 1 wherein the organic amine is selected from the group consisting of octylamine, octadecylamine, dihexylamine, trihexylamine, trioctylamine, ethanolamine, DL-1-amine-2-propanol, diisopropanolamine and triethanolamine.

10. The method of claim 1 wherein the organic amine constitutes about 5-10 percent by weight of the single phase aqueous treating solution.

11. The method of claim 1 wherein the water soluble film-forming polymer is selected from the group consisting of water soluble cellulose compounds and polyvinylpyrrolidone.

12. The method of claim 1 wherein the water soluble film-forming polymer is selected from the group consisting of methylcellulose, hydroxyethyl cellulose, hydroxypropyl methylcellulose, hydroxybutyl methylcellulose, hydroxypropyl cellulose and polyvinylpyrrolidone.

13. The method of claim 1 wherein the ratio of organic amine to polymer is in the range of 2:1 to 20:1.

14. The method of claim 1 wherein the carrier is selected from the group consisting of water, aqueous alcohol solution and aqueous glycol solution.

15. The method of claim 14 wherein the alcohol is ethanol or isopropanol and the glycol is propylene glycol.

16. The method of claim 1 wherein the single phase aqueous treating solution includes an additive selected from the group consisting of surfactants, antibacterial agents, anti-fungal agents, emollients, skin protectants and fragrances.

* * * * *

UNITED STATES PATENT AND TRADEMARK OFFICE
CERTIFICATE OF CORRECTION

PATENT NO. : 5,248,494
DATED : Sep. 28, 1993
INVENTOR(S) : Kuleza et al It is certified that error appears in the above-identified patent and that said Letters Patent is hereby corrected as shown below:

On title page, item [75] change "Lawrence Clifford M." to -- Clifford M. Lawrence --.

Column 10, line 30, change "4 - 8" to -- 4 - 18 --.

Column 10, line 36, change "DL-1-amine-2-propanol" to -- DL-1-amino-2-propanol --.

Column 10, line 56, change "is" to -- includes --.

Signed and Sealed this

Twelfth Day of April, 1994

Attest:

BRUCE LEHMAN

*Attesting Officer*  *Commissioner of Patents and Trademarks*